United States Patent [19]
Glorioso et al.

[11] Patent Number: 5,849,572
[45] Date of Patent: Dec. 15, 1998

[54] HSV-1 VECTOR CONTAINING A LAT PROMOTER

[75] Inventors: Joseph C. Glorioso, Cheswick, Pa.; David J. Fink, Ann Arbor, Mich.

[73] Assignee: Regents of the University of Michigan, Ann Arbor, Mich.

[21] Appl. No.: 411,920

[22] Filed: Mar. 28, 1995

Related U.S. Application Data

[63] Continuation of Ser. No. 995,842, Dec. 23, 1992, abandoned, which is a continuation of Ser. No. 856,868, Mar. 24, 1992, abandoned, which is a continuation of Ser. No. 595,041, Oct. 10, 1990, abandoned.

[51] Int. Cl.$^6$ .............................. C12N 15/00; C12N 7/00; C07H 21/04

[52] U.S. Cl. .................................... 435/320.1; 435/235.1; 536/24.1

[58] Field of Search .............................. 435/320.1, 235.1; 514/44; 95/32, 34; 536/24.1

[56] References Cited

U.S. PATENT DOCUMENTS 4,970,155  11/1990  Okasinski .

FOREIGN PATENT DOCUMENTS

| | | |
|---|---|---|
| 176170 | 4/1986 | European Pat. Off. . |
| 243155 | 10/1987 | European Pat. Off. . |
| 282330 | 9/1988 | European Pat. Off. . |
| 300422 | 1/1989 | European Pat. Off. . |
| 453242 | 10/1991 | European Pat. Off. . |
| 477056 | 3/1992 | European Pat. Off. . |
| WO 90/02551 | 3/1990 | WIPO . |
| WO 90/06757 | 6/1990 | WIPO . |
| WO 90/09441 | 8/1990 | WIPO . |
| WO 91/02788 | 3/1991 | WIPO . |

OTHER PUBLICATIONS

McGeoch et al (1985) J. Mol. Biol. 181, 1–13.
Frink et al (1983) J. Virol. 45, 634–647.
Wagner et al (1981) Proced. Natl. Acad. Sci. 78, 1441–1445.
Ace, C.I. et al., (1989) J. Virol. 63:2260–2269.
Anderson, J.R. et al., (1983) J. Neurol. Sci. 60:181–195.
Bak, I.J. et al., (1977) Brain Res. 136:415–429.
Bender, M.A. et al., (1987) J. Virol. 61: 1639–1646.
Boothman, D.A. et al., (1989) FEBS Lett. 258:159–162.
Chakrabarti, et al., (1985) Mol. Cell. Biol. 5:3403–3409.
Chiocca, E.A. et al., (1990) The New Biologist 2:739–746.
Clements, J.B. et al., (1977) Cell 12:275–285.
Cone, R.D. et al., (1987) Science 236:954–957.
Croen, K.D. et al., (1987) N. Engl. J. Med. 317:1427–1432.
Deatly, A.M. et al., (1987) Proc. Natl. Acad. Sci. (USA) 84:3204–3208.
Deatly, A.M. et al., (1988) J. Virol. 62:749–756.
Dixon, R.A.F. et al., (1980) J. Virol. 36:189–203.
Dobson, A. et al., (1990) Neuron 5:353–360.
Dobson, A. et al., (1989) J. Virol. 63:3844–3851.
Efstathiou, S. et al., (1989) J. Gen. Virol. 70: 869–879.
Efstathiou, S. et al., (1986) J. Virol. 57:446–455.
Fink, D.J. et al., (1990) Ann. Neurol. 28:220.
Fink, D.J. et al., (1990) Soc. Neurosci. Abstr. 16:964.
Frame, M.C. et al., (1987) J. Gen. Virol. 68:2699–2704.
Freese, A. et al., (1990) Biochem. Pharmacol. 40:2189–2199.
Friedmann, T., (1989) Science 244:1275–1280.
Geller, A. et al., (1988) Science 241:1667–1669.
Gorman, C.M. et al., (1982) Mol. Cell. Biol. 2:1044–1051.
Hill, J.M. et al., (1990) Virology 174:117–125.
Hill, T.J. (1985) in "The Herpesviruses" pp. 175–240. Plenum Press: New York.
Ho, D.Y. et al., (1989) Proc. Natl. Acad. Sci. (USA) 86:7596–7600.
Homa, F.L. et al., (1986) Mol. Cell. Biol. 6:3652–3666.
Homa, F.L. et al., (1988) Genes and Development 2:40–53.
Honess, R.W. et al., (1975) Proc. Natl. Acad. Sci. (USA) 72:1276–1280.
Honess, R.W. et al., (1974) J. Virol. 14:8–19.
Jalanko, A. et al., (1989) Gene 78:287–296.
Leib, D.A. et al., (1989) J. Virol. 63:2893–2900.
Mann, R. et al., (1983) Cell 33:153–159.
McFarland, D.J. et al., (1986) J. Neurol. Sci. 72:307–318.
Mellerick, D.M. et al., (1987) Virology 158:265–275.
Melton, D.W. et al., (1986) Cell 44:319–328.
Osborne, W.R.A. et al., (1988) Proc. Natl. Acad. Sci. 85:6851–6855.
Palella, T.D. et al., (1988) Mol. Cell. Biol. 8:457–460.
Palella, T.D. et al., (1988) Pediatr. Res. 24:129.
Palella, T.D. et al., (1989) Gene 80:137–144.
Patel, P.I. et al., (1986) Mol. Cell. Biol. 6:393–403.
Perry, L.J. et al., (1986) J. Gen. Virol. 67:2365–2380.
Puga, A. et al., (1987) J. Virol. 61:1700–1703.
Rixon, F.J. et al., (1990) J. Gen. Virol. 71:2931–2939.
Rock, D.L. et al., (1987) J. Virol. 61:3820–3826.
Rock, D.L. et al., (1983) Nature 302:523–525.
Sabel, B.A. et al., (1989) Soc. Neurosci. Abstr. 15:9.
Sanes, J.R. et al., (1986) EMBO J. 5:3133–3142.
Sauer, B. et al., (1987) Proc. Natl. Acad. Sci. (USA) 84:9108–9112.
Sederati, F. et al., (1989) J. Virol. 63:4455–4458.
Shapira, M. et al., (1987) Nuc. Acids Res. 15:3097–3111.
Shih, M. et al., (1984) Proc. Natl. Acad. Sci. USA 81:5867–5870.
Smiley, J.R. et al., (1987) J. Virol. 61:2368–2377.
Spivack, J.G. et al., (1987) J. Virol. 61:3841–3847.
Steiner, I. et al., (1989) EMBO J. 8:505–511.
Stevens, J.G. et al., (1987) Science 235: 1056–1059.
Van Zijl, M. et al., (1990) J. Gen. Virol. 71:1747–1755.
Wagner, E.K. et al., (1988) J. Virol. 62:1194–1202.
Weber, P.C. et al., (1988) Cell 54:369–381.
Weber, P.C. et al., (1987) Science 236: 576–579.
Post & Roizman (1981) Cell 25, 227–232.

*Primary Examiner*—Deborah Crouch
*Attorney, Agent, or Firm*—Leydig, Voit & Mayer, Ltd.

[57] ABSTRACT

A gene transfer vector for transferring genetic material to a host tissue and expressing a gene product therefrom includes a virus capable of establishing extra chromosomal viral latency in the host tissue. The strain includes at least one foreign gene recombined into the virus which is foreign to the viral genome and a promoter for initiating and driving transcription of the foreign gene during latency of the virus in the host tissue.

7 Claims, No Drawings

5,849,572

HSV-1 VECTOR CONTAINING A LAT PROMOTER

This is a continuation of application Ser. No. 07/995,842, filed Dec. 23, 1992, now abandoned, which in turn is a continuation of 07/856,868, filed Mar. 24, 1996, now abandoned, which is a continuation of 07/595,041, filed Oct. 10, 1990, now abandoned.

This invention was made with government support under Grant No. 1 R01 AI26937 awarded by the National Institutes of Health. The government has certain rights in the invention.

TECHNICAL FIELD

The present invention relates to a novel means for transferring foreign genetic material to a host tissue in vivo and the gene transfer vector for use therewith. The present invention further relates to methods of making such a gene transfer vector. The present invention also relates to a shuttle vector for introducing the foreign gene constructs into a recipient host genome and the method of utilizing the same for such a purpose.

More specifically, the present invention relates to the introduction of a virus latency vector as a gene transfer vehicle for the potential treatment of neurodegenerative disorders by gene therapy wherein the gene transfer vehicle is latent within the cells of the nervous system except for the expression of a single specific biologically active gene product.

BACKGROUND OF THE INVENTION

Gene replacement or augmentation therapy has been proposed as a viable alternative to pharmacotherapy and transplantation approaches for the treatment of neural disorders such as Parkinson's disease. This approach is based on the assumption that correction of a disease phenotype can be accomplished by the replacement of the mutant gene or the introduction of genetic material into cells defective in a particular gene product. For example, it is known that the tyrosine hydroxylase (TH) gene product and the enzyme aromatic amino acid decarboxylase are required for the production of dopamine. Thus, the introduction of the TH gene by this approach may be a plausible therapy for Parkinson's disease. Over the last decade, considerable work has been done in the area of constructing and developing gene delivery systems to accomplish such a therapeutic approach.

Viral vectors have been examined in great detail with respect to their use as a gene delivery system. The most widely used vector systems have been derived from both murine and avian retroviruses. Retroviruses are capable of infecting a wide variety of cells, and the viral genetic material of these viruses integrates into random sites within the cellular genome. Accordingly, cell replication and DNA synthesis is required to achieve integration of the genetic material. Additionally, many defective mutant virus strains already exist. Considerable work has centered around the development of helper cell lines that efficiently package the defective viral mutants (2,3,4). Many vectors exist that also contain a selectable marker such as that for neomycin resistance. Retroviral vectors have been used to introduce genes into a wide variety of cells (5–11) with particular emphasis placed on introduction of genes into hematopoietic cells.

Researchers have found several properties with the retroviral vector system that make it less than amenable for central nervous system (CNS) gene replacement. First, since retroviruses require replicating cells to achieve integration of the proviral genome, donor cells must first be transfected or infected with these vectors and then subsequently introduced as grafts into the CNS. There are several groups of researchers that are using this approach. However, this route of therapy is subject to the same problems that plague the simple transplantation therapeutic application. These problems include graft versus host and transplant rejection response, survival of the graft, and continued expression and regulation. The viral genomes of retroviruses are small and can reasonably accommodate the insertion of only 4 to 5 kb of foreign genetic material. Thus, these vectors are appropriate only for certain small single gene replacement therapies. For example, diseases such as Parkinson's disease, it may prove necessary to introduce both the TH gene and the decarboxylase gene in order to increase DA levels. This task can not be readily accomplished with a retroviral vector. The deficiencies of retroviral vector systems for gene transfer into the CNS do not exist for the herpes virus (HSV) vector.

HSV is a neurotropic virus, which in natural infection is taken up by axonal terminals and transported retrogradely to the neuronal cell body. In the neuronal cell body, the virus can establish long term persistence as latent, quiescent viral genomes (11). Latently infected neurons show an extremely restricted and characteristic pattern of viral gene expression (11). Focal HSV infection of specific brain regions can be achieved by stereotactic injection of small volumes of virus into specific brain regions (13,14). Since the HSV virus is a virus which can be targeted to neuronal tissues and is capable of naturally entering a latent state in which it expresses a limited portion of its genome, the HSV virus represents an ideal gene transfer vector for delivery of foreign genes into the CNS.

The HSV genome is a double stranded linear DNA molecule composed of two unique segments, each bracketed by inverted repeat sequences. The viral genes are regulated by a temporal cascade of gene expression (15,16,17). The three classes of HSV genes have been designated immediate early, delayed early, and late. The immediate early genes are located either with the repeat elements or directly adjacent to the repeats and are critical to the switching from latent to lytic infection. The immediate early genes are expressed to high levels upon infection in the absence of de novo protein synthesis and are the first lytic cycle viral genes to become active following reactivation from latency. In normal productive infections, the immediate early gene product ICP4 promoter is highly active and results in the production of high levels of ICP4 protein, the key transactivator of the early and late genes required for production of virion particles. Mutant viruses deleted in ICP4 are unable to carry out the replication cycle (18). Since expression of ICP4 results in disruption of the latent state, applicant postulated that blocking its expression should maintain latency.

The viral genome in latently infected neurons is present as either a circular or concatemeric extrachromosomal element (19,20,21). During latency the only transcriptionally active region of the viral genome maps to a segment of the inverted repeat sequences of $U_L$ just downstream of the ICP0 structural gene (22–27). The detected RNA species are transcribed off of the opposite strand from ICP0 and overlap a portion of the ICP0 coding sequence (22,27). Several RNA species have been detected from this region by Northern blot analysis. The main transcript is 1.8 to 2.3 kb in size and has been designated the latency associated transcript or LAT (24,26,27,28). Minor transcripts of 1.4 to 1.7 kb in size have also been found and represent spliced variants of the larger RNA species. Like viral RNAs, viral antigens present under lytic conditions are not detected in latently infected neurons (22). Several lines of evidence argue that LAT does not encode a protein. Antibodies to synthetic peptides representing an open reading frame located within LAT are unable to detect an LAT-specified protein in latently infected animals (28). Additionally, the LAT RNAs are located primarily within the nucleus of latently infected mouse neurons and are nonadenylated (22). Although these transcripts have been identified in neuronal tissue from both latently infected humans (29) and animals (30), deletion of sequences which encode LAT has no obvious effect on the ability of HSV to establish latent infections (31–35).

The sequence corresponding to the LAT promoter-regulatory region displays no basic homology to other HSV promoters (28) (See FIG. 1B)(SEQ ID NO:1). Although the sequence shows some degree of similarity to promoters active in neural tissue (36,37), specific consensus cis-regulatory elements are not apparent. Thus, this promoter is unique within the virus and may be related to cellular promoters which are active to normal neurons.

It can be concluded that the LAT promoter is unique within the virus and may be related to other promoters which are active in normal neurons. As discussed below, the unique transcriptional activity of LAT is proven to be important for expression of foreign genes in vivo. Over the past 15 years, applicants have been engaged in studies of the molecular biology of HSV replication and pathogenesis, including studies of the immunobiology of infection. The regulation of HSV gene expression has also been examined (38,39) and now includes studies of the role of specific promoter/regulator elements in viral growth and spread in brain cells. Applicant recently initiated an extensive probing of the HSV genome by insertional mutagenesis to map and characterize genes that contribute to neurovirulence and the molecular basis of HSV DNA replication and recombination (40,41). Applicants herein disclose an invention which was the culmination of understanding the molecular basis of HSV latency, its mechanism of establishment, maintenance and the events leading to virus reactivation. The natural outgrowth of these investigations is the development of HSV as a gene transfer vector for the nervous system, including the delivery and tissue specific expression.

More specifically, applicant has adopted a novel shuttle mechanism, adapted from the P1 phage cre-lox recombination system, to rapidly introduce foreign mini-gene cassettes into the virus genome in a site-directed manner. Upon introducing this aneuropathogenic recombinant viral construct into cells and maintaining the virus in its latent state while producing a desired gene product normally foreign to the virus, applicant will take the next step of utilizing this gene product to supplement an absent or lacking but otherwise necessary gene product of the host genome. Accordingly, the present invention can be utilized therapeutically for replacement therapy of neural disorders wherein the pathology is created by the absence of a gene product which can be replaced by literally the infection of the present invention.

SUMMARY OF THE INVENTION

In accordance with the present invention, there is provided a gene transfer vector for transferring genetic material to a host tissue and expressing a foreign gene product therefrom, the vector including a virus capable of establishing viral extra chromosomal latency in the host tissue. The virus includes at least one foreign gene recombined into the virus which is foreign to the viral genome and promoting means for initiating and driving transcription of the foreign gene during latency of the virus in the host tissue.

The present invention also, provides a method of transferring genetic material to a host tissue. The method generally includes the steps of introducing a virus into host tissue, establishing viral latency in the host tissue, and driving transcription of a foreign gene of the viral genome during latency of the viral strain in the host tissue.

In accordance with the present invention, there is further provided a method of making a gene transfer vector for transferring foreign genetic material to a host tissue, the method including the steps constructing of a viral genome to include at least one foreign gene capable of expressing a biologically active foreign product, identifying a promoter capable of driving expression of a gene during latency of the virus, and juxtaposing the promoter to the foreign gene for driving the expression of the foreign gene during latency of the virus in foreign host tissue.

Finally, the present invention provides a shuttle vector for introducing foreign gene constructs into a recipient host genome. The vector comprises a cell free system consisting of two DNA molecules, each of the DNA molecules including a lox site. One of these sites is a recipient host genome and the other of the sites is plasmid containing the foreign gene construct. A single protein consists of a recombinase specific for the lox site. The lox site in the recipient host genome provides a target for site specific recombination with the plasmid containing the foreign construct.

Other advantages of the present invention will be readily appreciated as the same becomes better understood by reference to the following detailed description:

DETAILED DESCRIPTION OF THE INVENTION

Generally, the present invention provides a gene transfer vector for transferring genetic materials to a host tissue, the vector including a virus capable of establishing extra chromosomal viral latency in the host tissue. That is, there is an absence of expression of the native viral gene proteins. The virus includes at least one foreign gene recombined into the virus which is foreign to the viral genome. Promoting means initiates and drives transcription of the foreign gene during latency of the virus in host tissue. Thus, the host cell function is not altered except by the expression of the gene(s) which is foreign to the viral genome. In other words, applicant has developed an aneurovirulent mutant strain which can establish life long latency in neurons of the CNS and express nonviral genes in a tissue specific manner. Applicant has engineered a virus which can replicate and establish latency in vivo without destroying neuronal target cells. By producing a biologically active gene product from the expression of the foreign gene during the latency of the viral strain in the host tissue, in combination with the viral strain not being pathogenic to the host tissue per se, applicant has created a mechanism by which pathologically nonproduced necessary cell maintaining factors can be manufactured intracellularly by the infecting strain to create normal cellular function and thereby cure the pathology. In a system where pathology is created by the absence of an otherwise normally produced growth factor, enzyme, or the like, the present invention can be utilized to manufacture that otherwise absent factor intracellularly, without creating damage to the host cells, to produce a soluble factor capable of systemic permeation.

By biologically active, it is meant that the gene product can function to correct an abnormal biological state of a tissue and result in the tissue functioning normally. This product could be an enzyme, a protein etc. The product could be eventually membrane bound or cytosolic. The product could reduce an abnormally high biological activity or increase an abnormally low biological activity.

For example, disorders such as Parkinson's and Alzheimer's disease are possibly the result of the age related absence of function of specific gene expression. It is expected that the present invention can be used to ameliorate the neurochemical and behavioral deficits that result from dopaminergic neurodegradation caused in 6-hydroxydopamine lesioned rats, these rats being an accepted model for Parkinson's disease. Further, it is expected that the present invention will also be useful in the study of and treatment of Alzheimer's disease, the disease being expected to be the result of a gene disfunction. In other words, the present invention will find utility in the study of and the potential cure for various diseases which can be traced to gene disorder and dysfunction wherein the gene can be made, through gene transfer consistent with the present invention, into an integral part of an engineered viral strain.

Applicant constructed a system wherein the host tissue is deficient of a gene product. The vector including the foreign gene product capable of expressing the gene product deficient in the host tissue includes a promoter specifically initiating and driving transcription of the foreign gene to express the deficient gene product during the latency.

The vector is an engineered strain of herpes simplex virus capable of replication in neuronal tissue of the nervous system without pathogensis and is capable of establishing latency in the nervous system tissue. The virus includes the foreign gene and the promoter for driving expression of the foreign gene during the latency of the virus.

The term latency is used herein to mean an extrachromasomal state wherein the foreign gene is expressed but the virus is not capable of replication. The virus cannot create a disease state but selective transcription of the foreign gene is driven. In essence, the virus incorporates the function and expression of the foreign gene into the host cell.

The promoter includes a latency transcription (LAT) promoter capable of initiating and driving transcription of the foreign gene in vivo from the nonhomologous ectopic site in the viral genome during latency of the virus in the neural tissue.

EXPERIMENTATION

To examine HSV latent infection within tissue of the nervous system of the mouse, applicant has developed a corneal scarification eye model of viral latency. Approximately $10^8$ pfu of virus is inoculated into the mouse following corneal scarification. Applicant has shown that these mice are healthy and do not shed virus. At four weeks post infection, the trigeminal ganglia (TG) are excised, full cell RNA are isolated and subjected to Northern blot analysis using a probe that is specific for the latency associated transcripts (LAT). Applicant detected a major transcript of 2.2 kb as well as minor transcripts of 1.6 and 0.9 kb, in agreement with the findings of others (43). Other HSV mRNAs were not detected, demonstrating that the LAT promoter is the only viral promoter active during latent HSV infection of mouse neural tissue, with similar results detected in rat peripheral nervous system. Applicant concluded that the LAT promoter is ideal to drive expression of foreign genes from the latent viral genome of recombinant constructs. This led applicant to characterize the LAT promoter and test its ability to express foreign genes during latency by insertion of the promoter-gene construct into a variety of genetic loci within the virus which results in alteration of viral pathogenesis.

The LAT RNA initiation site has been accurately mapped (28) and applicant anticipated that the promoter would be present upstream of that site. To locate the LAT promoter, the chloramphenicol acetyltransferase (CAT) reporter gene was inserted downstream of the putative LAT promoter at BamHI site that was introduced at a position 42 bp downstream of the RNA start site. This construct was assayed for CAT expression using transient transfection assays (42,43). Applicant has determined that the LAT promoter lies within a fragment extending from −598 to +42 relative to the LAT RNA start site. Contransfection experiments involving a plasmid carrying either the ICP0 or ICP4 gene and the LAT-CAT plasmid demonstrated that LAT promoter activity was reduced in the presence of these viral transactivators of lytic gene expression. These results showed that the LAT promoter was unique among other viral promoters in that it was repressed rather than induced by the viral transactivators (ICP0 and ICP4) of lytic genes. This result fits well with the finding that as the virus enters the latent state, ICP4 and ICP0 are no longer expressed and the LAT promoter becomes active signifying the establishment of the latent state. This interplay of the LAT promoter with the lytic cycle genes might be anticipated since LATp is the sole viral promoter active during viral latency. As discussed below, the next step was to determine whether this promoter was a moveable element which could be used to drive expression of nonviral genes in vivo from nonhomologous sites in the viral genome.

Viral recombinants with the LacZ reporter gene under the control of various promoters have been used to systematically evaluate the activity of those promoters in vivo, and to analyze the role of specific viral genes in the establishment of focal brain infection and the persistence of latency. Applicant tested eleven different viral constructs in vivo at times ranging from one day to four months after inoculation in 180 rats. The basic paradigm has been identical. Recombinant virus (1–5 µl containing approximately $10^8$ pfu/ml) was stereotactically injected into the hippocampus and striatum of 175 to 225 gram Sprague Dawley rats using a Kopf stereotactic frame and the coordinates defined in the Paxinos and Watson atlas (44) adjusted according to applicant's previous experience using dye injections. The rats were sacrificed at various times post injection by decapitation or perfusion, and cryostat or vibratome sections used for (1) reaction with X-gal to detect functional LacZ expression (45), (2) in situ hybridization (46) using a riboprobe specific for viral RNAs (gC, a lytic cycle gene; LAT, the latency-specific gene) to confirm the presence of HSV genomes in neurons, and (3) immunocytochemistry with anti-β-gal antibodies to confirm the presence of the β-gal protein and exclude the possibility of false positive X-gal staining from other enzymes which might cleave the substrate. Alternate sections from the same animals were stained with H&E or cresyl violet to evaluate pathologic changes and loss of neurons.

Focal injection is required because HSV infection after intracerebral injection causes asymmetric, widespread patchy infection of glia and neurons (47), while the infection after stereotactic injection is predictably localized (13,14). The hippocampus was first selected because of its characteristic histological organization and neuronal architecture which facilitate the determination of neuronal loss of damage due to the introduction of recombinant virus. Applicant chose the rat for three reasons. First, the size of the rat brain allows the injection of 1 μl volumes containing virus into discrete brain regions, while the size of the mouse brain would require substantially smaller injections. Second, wild-type HSV-1 is less neurovirulent in rats than in mice, so that restricted infection is more easily achieved. Additionally, a rat model of Parkinson's like disease can be readily achieved by depletion of dopaminergic neurons within the substantia nigra by treatment with 6-OHDA, and thus introduction of a recombinant HSV vector capable of expressing the TH gene from the latent viral genome can be evaluated as a gene replacement therapy. Finally, applicant has wide ranging experience in the use of the 6-OHDA treated rat as a model of nigrostriatal degeneration to include recently acquired experience with transplantation methodology.

Applicant engineered a virus which could replicate and establish latency in vivo without destroying neuronal target cells. Applicant first explored these genes as possible sites for disruption by integration of foreign mini-gene cassettes (40). One of these genes, Us3 contains domains highly homologous with serine kinases. The function of the kinase encoded by the Us3 gene is not known, but applicant had previously found a 4 log reduction in $LD_{50}$ by direct intracranial injection in mouse of a mutant virus carrying a Tn5 insertion within Us3 which completely blocks production of the Us3 gene product. The internal Tn5 sequence was replaced with the LacZ gene under the control of the viral late gene gC promoter. In this Us3::pgC-LacZ recombinant, the production of β-gal reflects foreign gene expression in the brain, and because the LacZ gene is driven by the gC promoter, LacZ expression is also indicative of active virus replication.

Due to the reduced neural pathogenicity of the Us3 mutant, the Us3::pgC-LacZ viral recombinant was used to examine foreign gene expression within rat CNS. X-gal staining of rats injected with Us3::pgC-LacZ showed marked blue reaction product in the injected hippocampus 2 to 5 days after inoculation, a time course consistent with productive infection. This staining extended throughout the dorsal hippocampus, at least 3 mm in a rostral-caudal direction. In sections counterstained with neutral red, it was apparent that blue cells were confined to the dentate gyrus, and semi-thin sections showed that the vast majority of cells with the X-gal reaction product were neurons. EM examination of ultrathin sections confirmed that the electron dense X-gal reaction product was predominantly in neurons, and also showed that those cells with X-gal reaction product in the cytoplasm contained viral particles in the nucleus. The specificity of the reaction product was further confirmed by immunoreactivity with an antibody to β-galatosidase and immunostaining with antibodies against an HSV-specific epitope (gC) which gave staining patterns identical to that seen with X-gal. In situ hybridization with probes for viral mRNA also showed a distribution similar to that seen with X-gal staining. Remarkably, this recombinant defective in Us3 did not appear to spread throughout the nervous system as observed with wild-type virus, where hippocampal neurons are destroyed in both brain hemispheres due to lytic replication and neuronal spread. X-gal staining, immunocytochemistry, and in situ hybridization studies all showed viral replication confined to the injected hippocampus. In addition, the recombinant virus caused only very limited disruption of the normal neuronal architecture of the hippocampus, in animals examined up to 10 months after inoculation. These findings indicate that the Us3 defective virus is special because it replicates in the CNS without obvious cell destruction. This virus is nonetheless lytic in vitro and therefore virus stocks can be readily produced without the necessity of growing the virus on a complementing cell line. Although there are large numbers of nonessential loci in the virus, none of these have been previously reported to have this special feature. Thus, Us3 is a potentially useful site for the introduction of foreign gene cassettes into the virus for effective gene transfer into the CNS.

In addition, it was important to determine whether the LAT promoter could be juxtaposed to a nonviral reporter gene and introduced back into the virus at a nonhomologous ectopic site to drive expression of this reporter gene after the virus established latency. Under these circumstances, no other viral genes would be expressed and the biological effects of the single foreign gene could then be assessed in cells harboring latent virus. In initial experiments applicant introduced the pLAT LacZ cassette into the gC structural gene, another gene nonessential for viral replication in vitro. gC::pLAT-LacZ recombinants injected into hippocampus proved to be significantly more pathogenic than the Us3 defective viruses. ⅔ of the rats injected with $5 \times 10^5$ pfu of gC::pLAT-LacZ died between 1 and 2 weeks after inoculation, compared to none of the Us3::pgC:LacZ injected animals. It was therefore necessary to introduce a second site mutation in the thymidine kinase gene by direct selection. Mutations within the tk gene were known to greatly reduce viral pathogenesis in the CNS. This same virus was also introduced into the animal by corneal scarification. At three days post infection viral proteins were detected in TG neurons by immunoperoxidase staining with polyclonal anti-HSV antiserum. By ten days post infection, however, no viral proteins could be detected. Rather, large numbers of blue neurons were detected by X-gal staining of TG sections, with staining increasing over time and present even at 6 months post inoculation. These results clearly demonstrated that the LAT promoter could be moved, reintroduced into the viral genome at a different locus and used to strongly express a foreign gene from the latent viral genome.

Because it was not known whether prior productive infection is a prerequisite for the establishment of latency following intracranial inoculation, applicant tested a d120 gC::pLAT-LacZ recombinant construct. The parental d120 virus is defective in the immediate early gene ICP4, which encodes an essential transactivator of early and late viral genes, and is therefore incapable of productive infection. Rats sacrificed three, five and seven days after inoculation with the d120 recombinant showed no evidence of X-gal staining and a milder inflammatory response than wild-type or the gC::pLAT-LacZ virus. Rats sacrificed three weeks after hippocampal inoculation showed individual intensely staining neurons scattered throughout cortical regions. However, due to the failure of this virus to infect a significant number of cells at the site of injection, it may not prove useful as a gene delivery vehicle. Similar problems were observed using a temperature sensitive mutant of ICP4 (tsK) to deliver an HSV-derived plasmid expressing LacZ (48), again underscoring the importance of the findings with the Us3 mutant.

In view of the above experimentation, applicant has developed a gene transfer vector as well as a method of transferring foreign genetic material to a host generally including the steps of introducing the above described engineered virus into the host tissue, establishing viral latency in the host tissue, and driving the transcription of the foreign gene from the viral genome during latency of the virus in the host tissue.

By expressing a soluble gene product from the foreign gene, the gene product is capable of reacting with cytosolic constituents in the host tissue. For example, if the gene product is an enzyme otherwise not present in the host tissue as the result of a gene defect, the gene product is capable of functioning as replacement therapy for the absent gene product having the capability of curing an otherwise pathogenic condition. By the gene product being soluble, it is capable of being released from the host tissue into the host system and therefore providing systemic therapy.

The experimentation further provides a method of making the gene transfer vector, generally, by engineering a viral genome to include at least one foreign gene capable of expressing the foreign gene product, identifying the promoter capable of driving transcription of the gene during latency of the virus, and juxtaposing the promoter to the foreign gene for driving the transcription of the foreign gene during latency of the virus in the foreign host tissue.

The present invention further provides a shuttle vector for introducing the foreign gene constructs into a recipient host genome. Accordingly, in order to facilitate the rapid introduction of applicants' foreign gene constructs into the HSV-1 genome, applicants have developed the novel shuttle vector mechanism based on the P1 phage cre-lox recombination system (49). This simple cell-free system requires only two DNA molecules each possessing a lox site, one the recipient viral genome and the other a plasmid containing the gene to be inserted, and a single protein molecule, the cre recombinase. HSV recombinants have been constructed in which the 34 nucleotide cis-acting lox site was inserted into the 5' end of the coding region of the viral thymidine kinase (tk) gene of other wild-type KOS virus (Ktk::lox2) or a glycoprotein B (gB) deficient virus (KΔT::lox 1). With both recombinants, the insertion of a lox site at the tk locus has made these viral recipients $tk^-$. Recent work demonstrated that tk mutants react poorly from the latent state (50,24,32), making the disruption of tk by insertion of the loxP site advantageous in the development of an HSV vector that enters and maintains permanent latency.

The lox site in the recipient viral DNA provides a target for site-specific recombination with a lox plasmid containing a test gene construct. This recombination is carried out in a cell free system using the P1 phage recombinase cre. The cell free recombination event is highly efficient, and at equilibrium, approximately 5% of the viral genomes represent recombinants. This simple system permits applicants to generate a large population of different recombinant virus genomes in a relatively easy fashion. Moreover, the plasmids up to 18 kb in length can be introduced into the viral genome without packaging problems. The genomic DNA is then transfected into appropriate cells for virus production. The transfection lysate is replated in the presence of X-gal and recombinants identified by their blue plaque phenotype due to the presence of the HCMV-LacZ gene cassette within the test plasmid. Moreover, plasmids of up to 45kb can be introduced into the viral genome.

As an example of the power of this technique, applicants have recently used this system to introduce a mutant form of gB into the gB recipient virus KΔT::lox1. The KΔT::lox1 recipient can only be maintained on a gB complementing cell line (D6). However, the new recombinant KΔT::102 produces blue plaques on normal Vero cells. Thus, applicants have been able to rescue a mutant in an essential viral gene product by reintroducing the wild-type gene into the genome by the cre-lox system.

In view of the above, applicants have shown viral constructs to express a foreign gene within neurons of the dentate gyrus during active infection after stereotactic injection into the hippocampus. In addition, the mutant strain showed limited neuro pathogenesis and no apparent spread within the nervous system following injection. Therefore, applicant has demonstrated a gene transfer vector, its method of use and manufacture, as well as a shuttle vector and its method of use, all of which having great utility in research and therapeutics.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed is:

1. A herpes simplex virus type 1 vector, capable of establishing latency, comprising
   (a) a latency active transcript promoter encoded by SEQ ID NO:1; and
   (b) a heterologous DNA sequence of interest operably linked to said promoter inserted within the genome of said HSV-1.

2. The vector of claim 1, wherein said latency active transcript promoter is located at a non-homologous ectopic site.

3. The vector of claim 1, wherein said DNA sequence is inserted at the site of the gC gene.

4. The vector of claim 1, wherein said DNA sequence expresses RNA.

5. The vector of claim 1, wherein said DNA sequence encodes a protein.

6. The vector of claim 5, wherein said DNA sequence encodes a decarboxylase.

7. The vector of claim 5, wherein said DNA sequence encodes a tyrosine hydroxylase.

* * * * *

UNITED STATES PATENT AND TRADEMARK OFFICE
CERTIFICATE OF CORRECTION

PATENT NO. : 5,849,572
DATED : December 15, 1998
INVENTOR(S) : Joseph C. Glorioso et al.

It is certified that error appears in the above-identified patent and that said Letters Patent is hereby corrected as shown below:

<u>Title page, Item [54] and Column 1, lines 1 and 2,</u>
In the Title, "HSV-1 VECTOR CONTAINING A LAT PROMOTER" should be -- HSV GENE TRANSFER VECTOR --.
Under Inventors, insert -- William F. Goins --.

<u>Column 1,</u>
Line 6, "Mar. 24, 1996" should be -- Mar. 24, 1992 --.

<u>Column 5,</u>
Line 32, "pathogensis" should be -- pathogenesis --.
Lines 36 and 37, "extrachromasomal" should be -- extrachromosomal --.

<u>Column 8,</u>
Line 52, after "regions." insert -- Applicants have also found that this virus cannot establish latency within the TG following corneal sacrification, but can do so if injected directly into the stroma or the posterior chamber of the eye. --.

Signed and Sealed this

Fourth Day of June, 2002

*Attest:*

JAMES E. ROGAN
*Attesting Officer*   *Director of the United States Patent and Trademark Office*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 697 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
CCTGCAGCCG GGGCGGCCAA GGGCGTCGGC GACATCCTCC CCCTAAGCGC CGGCCGGCCG    60
CTGGTCTGTT TTTTCGTTTT CCCCGTTTCG GGGGTGGTGG GGGTTGCGGT TTCTGTTTCT   120
TTAACCCGTC TGGGGTGTTT TTCGTTCCGT CGCCGGAATG TTTCGTTCGT CTGTCCCCTC   180
```

-continued

| | | | | | | |
|---|---|---|---|---|---|---|
| ACGGGGCGAA | GGCCGCGTAC | GGCCCGGGAC | GAGGGGCCCC | GACCGCGGCG | GTCCGGGCCC | 240 |
| CGTCCGGACC | CGCTCGCCGG | CACGCGACGC | GAAAAAGGCC | CCCCGGAGGC | TTTTCCGGGT | 300 |
| TCCCGGCCCG | GGGCCTGAGA | TGAACACTCG | GGGTTACCGC | CAACGGCCGG | CCCCCGTGGC | 360 |
| GGCCCGGCCC | GGGGCCCCGG | CGGACCCAAG | GGGCCCCGGC | CCGGGGCCCC | ACAACGGCCC | 420 |
| GGCGCATGCG | CTGTGGTTTT | TTTTTCCTCG | GTGTTCTGCC | GGGCTCCATC | GCCTTTCCTG | 480 |
| TTCTCGCTTC | TCCCCCCCCC | CTTCTTCACC | CCCAGTACCC | TCCTCCCTCC | CTTCCTCCCC | 540 |
| CGTTATCCCA | CTCGTCGAGG | GCGCCCCGGT | GTCGTTCAAC | AAAGACGCCG | CGTTTCCAGG | 600 |
| TAGGTTAGAC | ACCTGCTTCT | CCCCAATAGA | GGGGGGGGAC | CCAAACGACA | GGGGGCGCCC | 660 |
| CAGAGGCTAA | GGTCGGCCAC | GCCACTCGCG | GGTGGGC | | | 697 |